(12) United States Patent
Marzialetti et al.

(10) Patent No.: US 8,460,901 B2
(45) Date of Patent: Jun. 11, 2013

(54) FORMIC ACID TREATMENTS OF BIOMASS FEEDSTOCK

(75) Inventors: Teresita Marzialetti, San Pedro de la Paz (CL); Christopher W. Jones, Mableton, GA (US); Pradeep Agrawal, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 212 days.

(21) Appl. No.: 12/782,197

(22) Filed: May 18, 2010

(65) Prior Publication Data

US 2011/0287493 A1 Nov. 24, 2011

(51) Int. Cl.
- C12P 7/10 (2006.01)
- C12P 19/00 (2006.01)
- C13K 1/02 (2006.01)

(52) U.S. Cl.
USPC ............. 435/105; 435/72; 435/160; 435/165; 127/37; 44/451

(58) Field of Classification Search
USPC .......... 435/105, 72, 160, 165; 127/37; 44/451
See application file for complete search history.

(56) References Cited

U.S. PATENT DOCUMENTS

| 4,131,642 A | 12/1978 | Miller et al. |
| 6,252,109 B1 | 6/2001 | Rousu et al. |

FOREIGN PATENT DOCUMENTS

| WO | WO 2009/060126 | 5/2009 |
| WO | WO 2009/080737 | 7/2009 |
| WO | WO2009/092749 | 7/2009 |

OTHER PUBLICATIONS

Singh et al., "Kinetics and mechanism of the Ir(III)-catalyzed oxidation of xylose and maltose . . . ", 342 Carbohydrate Res. (2007), pp. 1078-1090.

Antal et al., "Mechanism of formation of 2-furaldehyde from D-xylose", 217 Carbohydrate Res. (1991), pp. 71-85.

Girisuta et al., "Kinetic Study of the Acid-Catalyzed Hydrolysis of Cellulose to Levulinic Acid", 46 Ind. Eng. Chem. Res. (2007), pp. 1696-1708.

Jin et al., "Formation of Formic Acid by Hydrothermal Oxidation . . . ", WaterDynamics: 5th Intl. Wrkshp. on Water Dynamics (Tohji et al., Eds), American Inst. of Physics (2008).

Kabyemela et al., "Glucose and Fructose Decomposition in Subcritical Water:.:", 38 Ind. Eng. Chem. Res. (1999), pp. 2888-2895.

Marzialetti et al., "Dilute Acid Hydrolysis of Loblolly Pine: A Comprehensive Approach", 47 Ind. Eng. Chem. Res. (2008), pp. 7131-7140.

Nimlos et al., "Energetics of Xylose Decomposition as Determined Using Quantum Mechanics Modeling", 110 J. Phys. Chem. (2006), pp. 11824-11838.

Paine et al., "Carbohydrate pyrolysis mechanics from isotropic labeling Part 2 . . . ", 82 J. Anal. Appl. Pyrolysis (2008), pp. 10-41.

Roman-Leshkov et al., "Phase Modifiers Promote Efficient Production of Hydroxymethylfurfural from Fructose", 312 Science (2006), pp. 1933-1937.

Singh et al., "Ruthenate ion catalysed oxidation of D-galactose and D-xylose by alkaline solution . . . ", J. Chem. Res. (May 2005), pp. 304-310.

Singh et al., "Kinetics of the Oxidation of D-Glucose and Cellobiose by Acidic Solution of N-Bromoacetamide . . .", 26 Chinese J. Chem. (2008), pp. 1057-1067.

Primary Examiner — Chih-Min Kam

(57) ABSTRACT

The instant invention pertains to the use of formic acid in new processes for treating feedstocks comprising holocellulose, as well as, new compositions suitable for, for example, bio-alcohol production. The processes may comprise first mixing the feedstock with an aqueous acid solution comprising formic acid and then producing a hydrolysis product comprising monosaccharides and water-soluble oligosaccharides. The compositions typically comprise a feedstock comprising holocellulose and an aqueous acid solution comprising formic acid. Advantageously, the processes and compositions of the present invention may be used in more environmentally friendly, cost-efficient production of fuels.

22 Claims, 7 Drawing Sheets

FORMIC ACID TREATMENTS OF BIOMASS FEEDSTOCK

FIELD OF THE INVENTION

The instant invention pertains to the use of dilute formic acid in new processes for treating feedstocks comprising holocellulose, as well as, new compositions suitable for, for example, bioalcohol production.

BACKGROUND AND SUMMARY OF THE INVENTION

In light of energy demand and environmental concerns, processes and compositions for the production of fuels from renewable feedstocks are needed. A common process involves producing ethanol from corn. Unfortunately, using corn and the like as precursors competes with food and feed supplies. Accordingly, other routes are being explored.

One such other route involves acid/hydrolysis of, for example, lignocellulosic biomass followed by, for example, fermentation to produce bioalcohols such as ethanol. Lignocellosic biomass refers to plant biomass that is composed of cellulose, hemicelluloses, and lignin. The carbohydrate polymers (cellulose and hemicelluloses) are tightly bound to the lignin. Lignocellulosic biomass can be grouped into four main categories: (1) agricultural residue (including corn stover and sugarcane bagasse), (2) dedicated energy crops, (3) wood residues (including sawmill and paper mill discards), and (4) municipal paperwaste. Unfortunately, many of these prior art approaches involve the use of or the producing a by-product of, for example, substances which may inhibit or poison heterogeneous catalysts such as noble metal catalysts that are sometimes used in downstream processing. Such substances include, for example, sulfuric acid, organic sulfur compounds, and/or halide ions. In some cases, the prior art approaches use, for example, mineral acids for acid hydrolysis of biomass. Unfortunately, these too may result in residual inorganic salt species and the like which can possibly affect the performance of downstream heterogeneous or enzyme catalysts. What's more, mineral acids may also be corrosive to conventional process equipment, may require the use of expensive alloys, and are generally not considered to be environmentally-friendly or green reagents. Unfortunately, other recent approaches such as those described in, for example, WO 2009/060126; WO 2009/080737; and 2009/092749 have one or more other disadvantages such as requiring concentrated acids or mixtures of acids, low yields, degradation of desirable products such as soluble monosaccharides, and/or complex processing conditions.

Accordingly, it would be desirable to discover new processes and compositions that could be employed in, for example, the production of fuels from renewable feedstocks. It would be advantageous if such processes and compositions did not require substances which may inhibit or otherwise affect the performance of downstream heterogeneous or enzyme catalysts. It would further be advantageous if the substances employed were less corrosive, more environmentally-friendly, effective at lower concentrations, and/or produced high yields without degrading desirable products and without the use of complex processing conditions.

Fortunately, the present inventors have discovered new processes and compositions which may meet one or more of the aforementioned needs or even have other advantages. In one embodiment, the invention relates to a process for treating a feedstock comprising holocellulose. The process comprises mixing the feedstock with an aqueous acid solution to form a mixture which has an initial pH at 25° C., i.e., $pH_{25° C.}$, of from about 1 to about 3. The acid comprises from about 1 to about 30 percent by weight based on the total weight of the aqueous acid solution. The acid is comprised of at least about 90% by weight of formic acid based on the total weight of the acid. Next, the mixture is subjected to conditions sufficient to produce a hydrolysis product comprising monosaccharides and water-soluble oligosaccharides. The sum of monosaccharides and water-soluble oligosaccharides is at least about 50% by weight of the total holocellulose in the feedstock.

In another embodiment, the invention relates to a composition suitable for bioalcohol production. The composition comprises a feedstock comprising holocellulose and an aqueous acid solution comprising at least about 90% formic acid based on total acid weight. The composition has a $pH_{25° C.}$ of from about 1 to about 3. The acid comprises from about 1 to about 30 percent by weight based on the total weight of the aqueous acid solution.

DETAILED DESCRIPTION OF THE INVENTION

Figure 1:
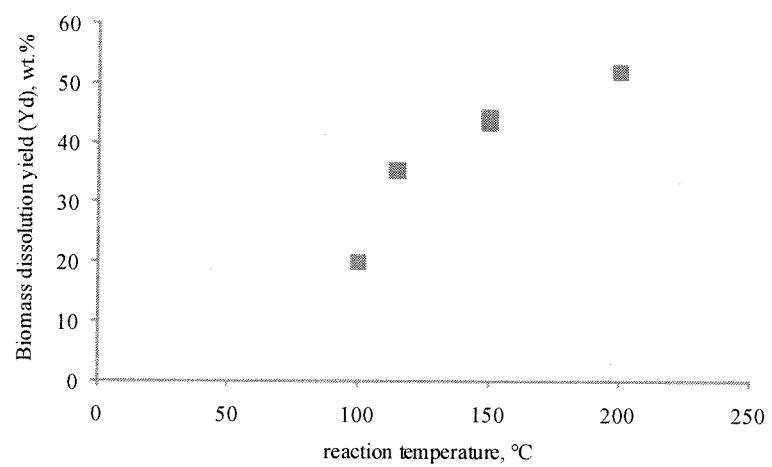
FIG. 1 shows switchgrass sawdust dissolution yield (wt. %) from acid hydrolysis using 8 wt. % formic acid ($pH_{25° C.}$=1.65) at different temperatures for 1 h.

The instant relates to the use of dilute formic acid in new processes for treating feedstocks comprising holocellulose, as well as, new compositions suitable for, for example, bioalcohol production.

Feedstock

The nature of the feedstock employed in the processes and compositions herein is not particularly critical so long as the feedstock comprises holocellulose. As used herein, "holocellulose" means the water-insoluble carbohydrate portion of a biomass, i.e., the portion of the biomass that is not lignin, extractives, or ash, but rather, includes substances such as polysaccharides. The precise composition of holocellulose may vary depending upon the specific feedstock employed. However, holocellulose useful herein typically contains varying amounts of celluloses such as alpha-cellulose and hemicellulose which comprise of various pentosan or hexosan polymers. Thus, virtually any lignocellulosic biomass may be employed as the feedstock in the processes and compositions of the instant invention.

In one embodiment a particularly preferable feedstock is a plant biomass. Biomass comes in many different types, which may be grouped into a few main categories: wood or forestry residues, including sawmill and paper mill discards, municipal paper waste, algae, agricultural residues, including corn stover (stalks and straw), and sugarcane bagasse, and dedicated energy crops, which are mostly composed of fast growing tall, woody grasses such as, for example, switchgrass. Any of the aforementioned may find use in the instant invention. A particularly preferable biomass comprises one with high holocellulose content, i.e., holocellulose content of greater than about 40 wt. %, preferably greater than about 60 wt. % weight percent of the biomass as measured by TAPPI 249.

Depending upon the nature of the feedstock it may be desirable to reduce at least a portion of it in size in order to expose additional surface area for treatment. Such reduction may be done in any convenient manner such as by grinding, cutting, chopping, etc. The desired size of the feedstock varies depending upon the type of ingredients and other specifics of the instant inventions. Typically, smaller size feedstocks may react quicker but cost more to produce. Generally, it is advantageous if the feedstock is reduced prior to hydrolyzing to a particle size of less than about 1 mm, preferably less than 0.6 mm, in its smallest dimension.

Similarly, it is often advantageous, or may even be necessary, in some situations to first condition at least a portion of the feedstock. By conditioning is meant to partially clean in order to remove at least some contaminants that may negatively affect downstream processes. This conditioning may assist in reducing or eliminating any undesired reactions in the following steps. The type of conditioning will depend upon the source of the feedstock, as well as, the amount and nature of the impurities and the following steps to which it will be subjected. Often, simple washing of the lignocellulosic feedstock is sufficient. Such conditioning, if done, may be accomplished prior to, in conjunction with, or subsequent to any size reduction. Additionally, if desired or advantageous, at least a portion or all of the feedstock that does not comprise holocellulose may be separated. However, this is unnecessary for many processes and conditions to which the composition will likely be subjected.

Aqueous Acid Solution

In addition to the feedstock, the compositions and processes of the instant invention employ an aqueous acid solution. The total amount of acid in the aqueous acid solution may vary depending upon the amount and type of feedstock employed, the amount and type of other ingredients, as well as, the conditions to which the composition comprising feedstock and aqueous acid solutions will be subjected. Typically, the aqueous acid solution comprises at least about 1, or at least about 4, or at least about 6 percent by weight of acid based on the total weight of the aqueous acid solution. On the other hand, the aqueous acid solution typically comprises less than about 30, or less than about 25, or less than about 20, or less than about 15 percent by weight of acid based on the total weight of the aqueous acid solution.

The type of acid or acids in the aqueous acid solution is not particularly critical so long as formic acid or a suitable derivative or equivalent thereof comprises at least about 80%, or at least about 85%, or at least about 90%, or at least about 95%, up to about 100% by weight of formic acid based on total acid weight. Other suitable acids besides formic acid may be included so long as the $pH_{25°C}$ is suitable for the desired process or composition. Typically, a suitable $pH_{25°C}$ of the mixture prior to hydrolyzing is at least about 1, or at least about 1.2, up to a $pH_{25°C}$ of at most about 3, or at most about 2. However, in many processes and compositions even though other acids may be included in the aqueous acid solution it may be beneficial in some situations to limit the amount of mineral acids since mineral acids may sometimes hinder some downstream processes. Therefore, in many cases, the acid of the aqueous acid solution is comprised of less than about 15% by weight, or less than about 10% by weight, or less than about 5% by weight, or less than about 1% by weight of mineral acid based on total aqueous acid solution weight. In a specific embodiment of the inventions, the acid comprises from about 4 to about 20% by weight of acid solution, and the acid is comprised of at least about 95% by weight of formic acid based on the total weight of the acid.

Origin of Formic Acid

While the formic acid employed in the aqueous acid solution may be of any origin, in one embodiment of the invention the formic acid is produced from a renewable biomass feedstock. In this manner, if desired, an integrated hydrolysis process may be employed wherein the formic acid used in treating biomass is also generated by biomass. For example, at least a portion of the formic acid employed as the aqueous acid may be produced in a method comprising a step selected from the group consisting of acid hydrolyzing one or more carbohydrates, pyrolyzing glucose, and oxidizing one or more monosaccharides. Of course, combinations of the aforementioned steps may also be employed.

Such steps have been described previously. For example, formic acid may be produced by acid hydrolysis of carbohydrates as reported in, for example, Roman-Leshkov, Y., J. N. Chheda, and J. A. Dumesic, *Phase modifiers promote efficient production of hydroxymethylfurfural from fructose*. Science, 2006. 312(5782): p. 1933-1937; Kabyemela, B. M., et al., Glucose and fructose decomposition in subcritical and supercritical water: Detailed reaction pathway, mechanisms, and kinetics. Industrial & Engineering Chemistry Research, 1999. 38(8): p. 2888-2895; and Nimlos, M. R., et al., *Energetics of xylose decomposition as determined using quantum mechanics modeling*. Journal of Physical Chemistry A, 2006. 110(42): p. 11824-11838.

Pyrolysis of glucose to make formic acid has been described in, for example, Paine, J. B., Y. B. Pithawalla, and J. D. Naworal, *Carbohydrate pyrolysis mechanisms from isotopic labeling. Part 2. The pyrolysis of D- glucose: General disconnective analysis and the formation of C-1 and C-2 carbonyl compounds by electrocyclic fragmentation mechanisms*. Journal of Analytical and Applied Pyrolysis, 2008. 82(1) 10-41.

Oxidation of monosaccharides to prepare formic acid in various processes has also been described. For example, the formation of formic acid by hydrothermal oxidation of glucose is described in Jin, F. Y., J.; Li, G.; Kishita, A.; Tohji, K.; Enomoto, H., *Formation of formic acid by hydrothermal oxidation of carbohydrate biomass for producing hydrogen*. AIP Conference Proceedings, 2008. 987(Water Dynamics): p. 139-142 and the oxidation of carbohydrates using transition metal complex species as catalysts has also been reported by, for example, Singh, A. K., et al., *Ruthenate ion catalysed oxidation of D-galactose and D-xylose by alkaline solution of sodium metaperiodate: a kinetic study*. Journal of Chemical Research-S, 2005(5): p. 304-310; Singh, A. K., et al., *Kinetics and mechanism of the Ir(III)-catalyzed oxidation of xylose and maltose by potassium iodate in aqueous alkaline*

*medium*. Carbohydrate Research, 2007. 342(8): p. 1078-1090; and Singh, A. K. S., Jaya; Srivatsava, Shalini; Rahmani, Shahla., *Kinetics of the oxidation of D-glucose and cellobiose by acidic solution of N-bromoacetamide using transition metal complex species*, [RuCl$_3$(H$_2$0)$_2$OH]—, *as catalyst* Chinese Journal of Chemistry 2008. 26(6): p. 1057-1067.

Initial Compositions of Feedstock and Aqueous Acid Solution

The compositions of the above-described feedstock and aqueous acid solution may be prepared in any convenient manner. Typically, appropriate types and amounts of the feedstock and aqueous acid solution may be simply mixed under ambient conditions. The volume/weight ratio of aqueous acid solution to feedstock will vary depending upon the type of ingredients and subsequent processing steps. Typically, however the volume/weight ratio of aqueous acid solution to feedstock is at least about 5, or at least about 10, up to at most 12, or at most 15 at 25° C.

In one specific embodiment of the instant invention, the composition employed consists essentially of a lignocellulosic feedstock, formic acid, and water in the liquid with the previously mentioned volume/weight ratio of aqueous acid solution to feedstock. That is, formic acid (and perhaps minor amounts of other similarly non-corrosive acids that do not substantially inhibit downstream heterogeneous or enzyme catalysts) make up nearly the entirety of the acid content of the aqueous acid solution. In this manner, downstream processing, as well as, processing equipment is not substantially hindered by, for example, large amounts of mineral acids.

Processes Involving the Initial Compositions of Feedstock and Aqueous Acid Solution Such as Acid Hydrolysis The initial compositions of feedstock and aqueous acid solution may be used in any number of advantageous processes. For example, in an acid hydrolysis of, for example, a feedstock described above, one may first form a mixture of feedstock and an aqueous acid solution which has an initial $pH_{25° C.}$ of from about 1 to about 3, wherein the aqueous acid solution comprises from about 1 to about 30 percent by weight of acid based on the total weight of the aqueous acid solution and wherein said acid is comprised of at least about 80%, or at least about 85%, or at least about 90%, or at least about 95%, up to about 100% by weight of formic acid based on the total weight of the acid. The amounts of feedstock and acid may be, for example, in the volume/weight ratios of aqueous acid solution to feedstock described above.

This mixture may be subjected to conditions sufficient to produce a hydrolysis product comprising monosaccharides and water-soluble oligosaccharides. As used herein, the term "monosaccharide" means a molecule with the chemical structure H(CHOH)$_n$C=O(CHOH)$_m$H wherein n, and m are integers of 0 or more. Examples of monosaccharides include, for example, glucose (dextrose), arabinose, fructose (levulose), galactose, xylose, mannose, and ribose. The term "water-soluble oligosaccharide" as used herein means an oligomeric saccharide comprising at least two monosaccharide units which oligomeric saccharide dissolves in water at room temperature and a $pH_{25C}$ of 2. Advantageously, in many instances the sum of monosaccharides and water-soluble oligosaccharides may be at least about 50% by weight, or at least about 60 wt. %, or at least about 70 wt. % of the total holocellulose in the feedstock.

Such hydrolyzing conditions may vary depending upon the amount and type of feedstock, nature and concentration of acid, $pH_{25° C.}$, etc. Suitable conditions generally include subjecting the mixture to an increased temperature for a sufficient time to form the desired products without degrading the desired products. Such temperatures may typically be at least about 75° C., or at least about 100° C., or at least about 125° C. and less than about 225° C., or less than about 200° C., or less than about 175° C. The amount of time to which the mixture should be subjected to the increased temperature will generally be less as the temperature is increased. Generally, such times are at least about 20, or least about 30, or at least about 45 minutes but less than about 3 hours, or less than about 2 hours, or less than about 1.5 hours. In one embodiment, the mixture is hydrolyzed at a temperature of from about 75° C. to about 225° C. for a time period of from about 30 minutes to 3 hours. In another embodiment, the mixture is hydrolyzed at a temperature of from about 125° C. to about 175° C. for a time period of from about 45 minutes to 2 hours. This process often leads to a product comprising, among other substances, monosaccharides, water-soluble oligosaccharides, HMF, and furfural. Advantageously, one of skill in the art with the benefit of this disclosure may vary the conditions to adjust the relative proportions of monosaccharides, water-soluble oligosaccharides, HMF, and furfural depending upon the further processing, if any, that will be employed.

Recycle of Formic Acid

Generally, the aqueous formic acid solution employed in the inventive process may be recovered and/or recycled after the acid hydrolysis if desired so long as the formic acid has not been converted to another form. Any suitable recovery technique may be employed and suitable techniques include, for example, distillation, as well as, vaporization of formic acid in the form of methyl formate as described in, for example, U.S. Pat. No. 4,131,642. If chemically bound formic acid is to be removed from a material containing the same, then techniques such as those described in, for example, U.S. Pat. No. 6,252,109 may be employed. For any formic acid which may be converted to a formate salt such as sodium formate, then a neutralization reaction may be desired with, for example, sulfuric acid to bring the pH down to 3.5 or less and convert the formate back to formic acid. Such procedures are described in, for example, U.S. Pat. No. 4,131,642 and generally follow the following reaction: 2HCO$_2$Na+H$_2$SO$_4$→2HCO$_2$H+Na$_2$SO$_4$.

Further Processing Such as Enzymatic Hydrolysis or Fermentation

Advantageously, any number of further processing steps may be employed to make useful products. As but one example, at least a portion of water-soluble oligosaccharides may be converted to monosaccharides such as glucose. This can be accomplished in any convenient manner such as enzymatic hydrolysis. Of course, at least a portion to all of the monosaccharides such as glucose obtained in any acidic hydrolysis and/or enzymatic hydrolysis may be fermented under suitable conditions to form ethanol, butanol, or a mixture thereof which is useful as a biofuel.

When conducting such further processing it may be beneficial to remove at least a portion to all of the solids from the product prior to said enzymatic hydrolysis. The solid may be separated from the liquid in any convenient manner for further processing. Such separation manners include, for example, filtration, centrifugation, and the like. These solids or hydrolyzate residues may be suitable for further reaction with, for example, hydrogen in the presence of a catalyst to yield an energy source. If desired, the hydrolyzate residue and/or energy source may be at least partially to fully deoxygenated. In this manner, fuels more suitable for transportation are often obtainable.

Although only exemplary embodiments are specifically illustrated and described herein, it will be appreciated that many modifications and variations of the process and apparatus described herein are possible in light of the above teachings and within the purview of the appended claims without departing from the spirit and intended scope of the claimed subject matter.

EXAMPLE 1

Switchgrass Feedstock Acid Dissolution

The below example employs switchgrass feedstock dissolution using aqueous acid solutions of various types and concentrations. The aqueous acid solutions comprising formic acid of the present inventions were found to exhibit surprising and unexpected dissolution efficiency, monosaccharide yield, and 2-furaldehyde /5-hydroxymethyl-2-furaldehyde yields.
Materials and Methods Six monosaccharides were used as standards for carbohydrate analysis: glucose, arabinose, galactose, xylose, mannose and fructose. All were purchased from Aldrich. Further dehydration of monosaccharides was quantified by identifying and analyzing two degradation products: 2-furaldehyde (furfural) and 5-hydroxymethyl-2-furaldehyde (HMF), both compounds purchased from Aldrich. Various acid-hydrolysis solutions were prepared using sulfuric acid (Fisher Scientific), trifluoroacetic acid (EMD Chemicals), acetic acid (EMD Chemicals) and formic acid (EMD Chemicals). The water used in all experiments was de-ionized (DI) water at $pH_{25°C.}$~5.4. Switchgrass was received as stalks of about 3 ft in length and 5 mm in the diameter, with around 2 mm pith diameter. The stalks were milled using a Wiley Mill. The fraction corresponding to −25+60 mesh was used for the examples.
Experimental Procedure
Acid Hydrolysis Reactions All reactions were performed in a 300 mL Parr reactor equipped with a glass liner. The corresponding dilute-acid solution and the untreated raw material were weighed in the glass liner of the reactor. A liquid to dry wood ratio of 9 (L/W=9) was used in all tests. A typical mass of switchgrass sawdust used was 10 g, of which ~8% was moisture. The liner with the wood and the liquid was placed into the reactor, and the reactor was closed and heated to the desired reaction temperature. After the reaction, the reactor was cooled and slowly depressurized as needed. The liner contents were emptied into a vacuum filtration apparatus. Two aliquots of the liquid sample were collected from the filtrate for HPLC and HPAEC analyses. The solid residue was washed with deionized water, and two aliquots of the wash liquid were collected for HPLC and HPAEC analyses. All liquid samples were sealed in a vial and stored closed in a freezer, at −5° C., to limit further reactions. The solid residue was collected in a clean, pre-weighed Petri dish and put in an oven at 105° C. overnight. All dried solid residue samples were then weighed at room temperature with a precision balance, and they were stored in a refrigerator until further characterization.

The reaction temperatures tested were 100° C., 120° C., 150° C., and 200° C. The starting $pH_{25°C.}$ of the acid solutions was 1.65 (representing ~8 wt. % formic acid) and 1.07 (representing ~30 wt. % formic acid). The reaction hold time at the reaction temperature after the heating ramp was 1 hr. The heating and cooling times of the reactor were not reported as part of the reaction time.
Enzymatic Hydrolysis (EH) of Liquid Product After acid hydrolysis, an aliquot of the liquid product was separated for enzymatic hydrolysis to hydrolyze water-soluble oligosaccharides and quantify monosaccharides as described in Marzialetti, T., et al., *Dilute acid hydrolysis of Loblolly pine: A comprehensive approach*. Industrial & Engineering Chemistry Research, 2008. 47(19): p. 7131-7140. The $pH_{25°C.}$ of these samples was adjusted to 6 using a solution of 50 mM of sodium acetate (NaOAc) as buffer. Three commercial enzymes were used in these experiments: cellulase mixture (endo+exoglucanase+β-glucosidase) to hydrolyze poly-glucose units, an excess of β-Glucosidase to break down cellobiose, and xylanase (endo-1,4-β-Xylanase) to help breakdown xylan. 0.168 mL of cellulase, 0.084 g of β-glucosidase and 0.500 g of xylanase were placed in pressure tubes followed by the addition of 1.5 mL of liquid sample at $pH_{25°C.}$=6 and 12.5 mL of DI water. Then, the pressure tubes were immersed in a silicon oil bath at 35° C. for 1 hr.
Biomass Preparation and Analytical Procedure Switchgrass sawdust feedstock was milled and sieved with the −25+60 mesh fraction of sawdust stored in zipped bags in a freezer until they were used in experiments. The raw material was not treated before reaction, so it was not extractive free. The moisture of the feedstock (8.5%) was measured using a Moisture Analyzer/balance (Mettler-Toledo HB43 moisture balance). The ash content was determined by heating a sample at 525° C. for 2 hours in accordance with TAPPI T211 om-93. The extractives were obtained following the procedure described in TAPPI T 264 cm-97, using dichloromethane treatment for 24 hours in a Soxhlet apparatus. Acid-soluble and acid-insoluble lignin were obtained following the method outlined in TAPPI T222 om-98. In this method, the raw material sawdust was hydrolyzed using 72% $H_2SO_4$ solution. The insoluble residue was filtered and weighed, determining the Klason lignin by mass difference. The acid-soluble fraction of lignin was then determined by a spectrophotometric method based on absorption of ultraviolet radiation. The monosaccharides dissolved in the aqueous phase such as glucose, arabinose, galactose, xylose, mannose and fructose were measured using the procedure described in TAPPI T 249. Accordingly, after the acid hydrolysis of the raw material described above, the liquid product obtained after filtration was analyzed for monosaccharide content using high-performance anion-exchange chromatography with a pulsed amperometric detector (HPAEC-PAD, Dionex) and a CarboPac PA10 column. The carbohydrate analyses include an internal sugar standard, fucose, which is not found in the biomass used in this study and thus serves as a calibration standard. The monosaccharide degradation products were characterized using a Shimadzu HPLC model (LC Avp-10) employing 0.005N $H_2SO_4$ as the eluent.
Calculations and Characterization of Raw Material Biomass dissolution yield ($Y_d$, wt. %) was determined using Equation 1 by weighing oven-dried raw material and oven-dried solid residue:

$$Y_d = \frac{m_{dry\text{-}raw\text{-}material} - m_{dry\text{-}residue}}{m_{dry\text{-}raw\text{-}material}} \cdot 100 \qquad \text{Equation 1}$$

The soluble monosaccharide content (m, mg) was calculated using the HPAE chromatograph described above; therefore, Equation 2 defines the yield of monosaccharides wt. %) derived from either hydrolyzed cellulose or hydrolyzed hemicellulose:

$$Y_{soluble\text{-}monosaccharide}(Y_m) = \frac{m}{m_{dry\text{-}raw\text{-}material}} \cdot 100 \qquad \text{Equation 2}$$

Similarly, the yields of furfural and HMF ($Y_{dp}$, wt. %) were calculated using Equation 2, based on measurements of the furfural and HMF content (m, mg) made using liquid chromatography, as mentioned above. According to the formation mechanisms proposed in the literature such as Girisuta, B., L. Janssen, and H. J. Heeres, *Kinetic study on the acid-catalyzed hydrolysis of cellulose to levulinic acid*. Industrial & Engineering Chemistry Research, 2007. 46(6): p. 1696-170 and Antal, M. J., Leesomboon, T., Mok, W. S., and Richards, G. N., *Kinetic-studies of the reactions of ketoses and aldoses in water at high-temperature 0.3. Mechanism of formation of 2-furaldehyde from D-xylose*. Carbohydrate Research, 1991. 217: p. 71-85., the dehydration of one mole of pentose yields one mole of furfural after losing three water molecules. Likewise, one mole of hexose produces one mole of HMF. Schemes 1 and 2 below represent the acid-hydrolyzed dehydration of hexoses and pentoses, respectively. Table 1 summarizes composition of raw material determined according to the methods mentioned above.

Scheme 1: Acid-catalyzed dehydration of glucose (hexoses) to levulinic acid and formic acid with HMF as detectable intermediate.

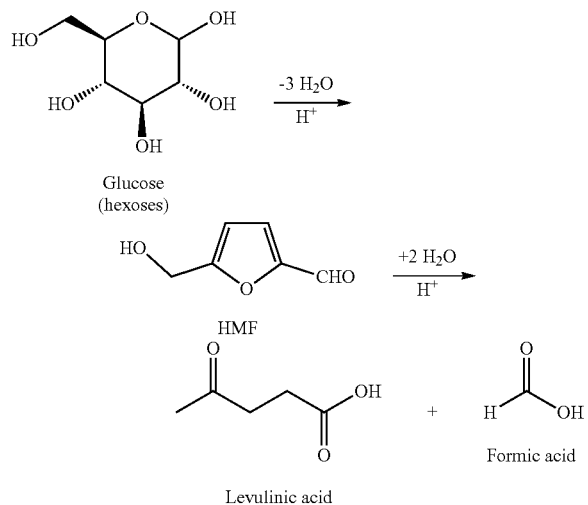

Scheme 2: Acid-catalyzed dehydration of xylose (pentoses) to furfural.

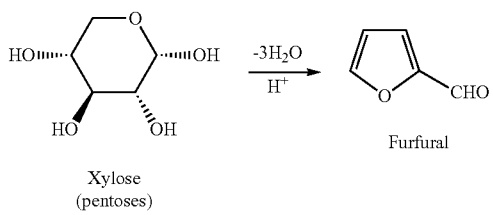

TABLE 1

Composition of switchgrass sawdust feedstock

| Monosaccharide | $\dfrac{m}{m_{dry\text{-}raw\text{-}material}} \cdot 100$, wt. % |
|---|---|
| Glucose | 33.9 |
| Arabinose | 3.7 |
| Galactose | 1.5 |
| Xylose | 23.9 |
| Mannose | 0.6 |
| Total | 63.6 |
| Extractives and ash | 5.8 |
| acid insoluble lignin (Klason) | 3.3 |
| acid soluble lignin | 21.4 |
| Closed balance | 94.1 * |

* These values are the average calculated from two separate analyses in which both values differ in less than 5% from each other. The composition table does not include all species present in the raw material such as proteins, uronic acid and acetyl components of the hemicelluloses.

Results and Discussion

Effect of Temperature and of Acid Concentration in Dilute Formic Acid Hydrolysis of Switchgrass The acid hydrolysis of switchgrass sawdust was investigated at temperatures between 100° C. and 200° C. for 1 h using dilute formic acid at an initial $pH_{25°C.}$ of 1.65. Biomass dissolution yield (wt. %), as represented in FIG. 1, showed an increase when raising the reaction temperature. At 200° C., the biomass dissolution yield was 52 wt. %, suggesting complete hydrolysis of solid hemicellulose and a high degree of hydrolysis of solid cellulose. Considering that total carbohydrate content of the raw material was 63.6 wt. % (based on dry-raw material, see Table 1), ~82 wt. % of carbohydrate fraction of switchgrass was dissolved at 200° C. and $pH_{25°C.}$=1.65 (8 wt. % of formic acid).

In a preceding study by Marzialetti, T., et al., *Dilute acid hydrolysis of Loblolly pine: A comprehensive approach*. Industrial & Engineering Chemistry Research, 2008. 47(19): p. 7131-7140, the presence of water-soluble oligosaccharides in the liquid product from acid hydrolysis was confirmed by applying a subsequent acid hydrolysis to the solid-free liquid hydrolysate (liquid product from the acid hydrolysis of raw material). This subsequent hydrolysis was performed following the NREL procedure with 4% $H_2SO_4$ for 1 h at 121° C. The carbohydrate analysis of this liquid product showed an increase in soluble monosaccharide yield compared with the primary acid hydrolysis, confirming the presence of water-soluble oligosaccharides in the original acid hydrolysis. However, this subsequent acid hydrolysis of the liquid sample also dehydrates some of the monosaccharides present in solution. Thus, a subsequent acid hydrolysis of the liquid product from acid hydrolysis of raw material typically does not allow quantification of the exact amount of water-soluble oligosaccharides due to likely monosaccharide degradation in series reactions.

Pursuing quantification of water-soluble oligosaccharides in the acid hydrolysis liquid sample, the acid hydrolysis liquid sample was treated using a mixture of enzymes that selectively hydrolyze oligosaccharides without significant side reactions. Three commercial enzymes were used in these experiments: cellulase mixture, an excess of β-Glucosidase and xylanase. The enzymatic hydrolysis tests were performed at 35° C. for 1 hr in pressure tubes heated by a silicon oil bath. The pH of those samples was adjusted to 6 using a solution of 50 mM of sodium acetate (NaOAc) as buffer.

Figure 2:
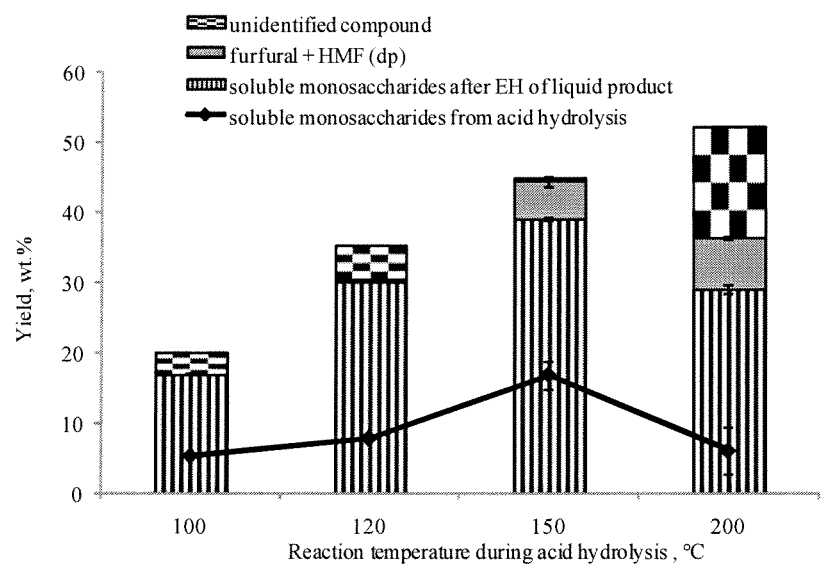
FIG. 2 shows water-soluble monosaccharide yield, degradation product yield (furfural and HMF) and unidentified compounds from acid hydrolysis. The error bars represent the range of numbers obtained from multiple runs.

It was observed that the soluble monosaccharide concentration increased substantially after enzymatic hydrolysis of the liquid products from acid hydrolysis of switchgrass sawdust, indicating the presence of oligosaccharides in the original samples and allowing monosaccharides to be completely quantified as shown in FIG. 2. This data shows that monosaccharides production (both after and before enzymatic hydrolysis) increased in the temperature range from 100° C. to 150° C., but decreased significantly at 200° C. This decrease in the soluble monosaccharide yield at high temperature suggests additional degradation (dehydration reactions) of monosaccharides in series reactions (e.g. Schemes 1 and 2, as well as other possible pathways), which is reflected not only in the increased degradation products yield (furfural+HMF), but also as unidentified product category (FIG. 2).

The unidentified liquid products substantially increased at high temperature (200° C.) suggesting further degradation of furfural and HMF into unidentified organic products (see Scheme 1). However, at low temperatures, there may be small amount of unreacted water-soluble oligosaccharides, since enzymatic hydrolysis conditions were not optimized for each sample tested. The unidentified compounds were calculated as the difference between biomass dissolution yield and the sum of monosaccharides yield after enzymatic hydrolysis of liquid product, and of degradation product yield.

Additional experiments were carried out using formic acid at three different acid concentrations, 8 wt. % ($pH_{25°C.}$=1.65), 30 wt. % ($pH_{25°C.}$=1.08) and 80 wt. % of acid based on the total weight of aqueous acid solution. Here, biomass dissolution yield increased from 52 wt % to 56 wt. % (see Table 3) with increasing acid concentration from 8 wt. % ($pH_{25°C.}$=1.65) to 30 wt. % ($pH_{25°C.}$=1.08) at 200° C. Nevertheless, soluble monosaccharide yield decreased when the acid concentration increased (see Table 3) because of monosaccharide dehydration in acidic media. In the experiments, 60 wt % of the raw switchgrass is sugars (Table 1); consequently, entry 5 in Table 2 suggests that 93 wt. % of monosaccharides from switchgrass was dissolved when acid hydrolysis was carried out at $pH_{25°C.}$=1.08 and 200° C.

TABLE 2

Experimental conditions and yields of acid hydrolysis of switchgrass feedstock tested using 8 wt. %, 30 wt. % and 80 wt. % of formic acid.

| Entry | Temperature, °C. | Time, h | Formic acid, wt. % | Biomass dissolution yield (Yd), wt. % | Monosaccharides yield ($Y_m$), wt. % |
|---|---|---|---|---|---|
| 1 | 100 | 1 | 8 | 20 | 17 |
| 2 | 150 | 1 | 8 | 44 | 39 |
| 3 | 200 | 1 | 8 | 52 | 29 |
| 4 | 150 | 1 | 30 | 50 | 43 |
| 5 | 200 | 1 | 30 | 56 | 22 |
| 6 | 100 | 1 | 80 | 53 | 36 |
| 7 | 150 | 1 | 80 | 52 | 15 |

Using concentrated formic acid (80 wt. %), biomass dissolution yield substantially increased when the reaction temperature was 100° C., but decreased at higher temperature (150° C.) suggesting a re-polymerization process may have occurred. Besides the reduced biomass dissolution yield compared to the use of more dilute acid, highly concentrated formic acid has the disadvantage of increased acid cost, and possible additional costs for corrosion-resistant materials of construction. Thus, the relatively dilute formic acid concentrations used in the present inventions often have high efficiency and good performance in dissolving feedstocks comprising holocellulose such as switchgrass sawdust.

Reproducibility

Figure 3:
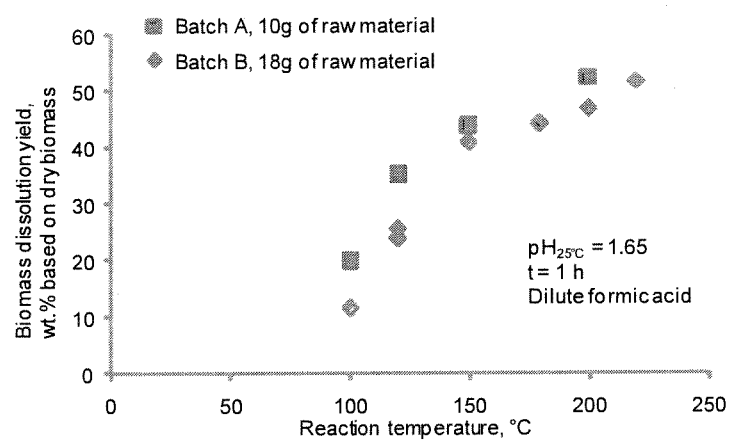
FIG. 3 shows biomass dissolution yield from the acid hydrolysis of switchgrass sawdust using 8 wt. % formic acid ($pH_{25° C.}$=1.65) on batch A (10 g of raw material) and on batch B (18 g of raw material).

The acid hydrolysis of switchgrass sawdust was also tested on a slightly different scale using 18 g of raw material, using the same reactor, to evaluate the reproducibility of the process. Following acid hydrolysis using 8 wt. % formic acid ($pH_{25°C.}$=1.65), the solid-free solutions were reacted by enzymatic hydrolysis to hydrolyze water-soluble oligosaccharides, as noted above. FIG. 3 represents a comparison between the biomass dissolution yield of both processes on two batches: batch A using 10 g of raw material, and batch B using 18 g of raw material. The biomass dissolution yield had a similar trend in both processes, increasing with the reaction temperature.

Figure 4:
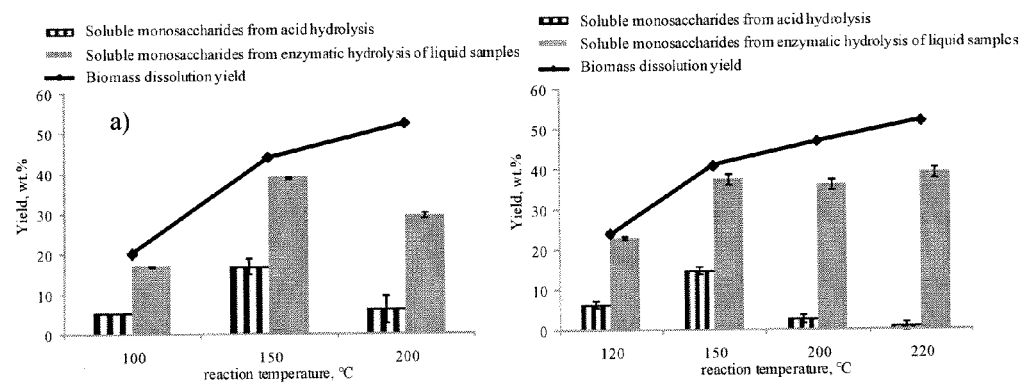
FIG. 4 shows biomass dissolution yield and water-soluble monosaccharide yield from both liquid product of acid hydrolysis switchgrass sawdust using 8 wt. % formic acid ($pH_{25° C.}$=1.65) and enzymatic hydrolysis of solid-free liquid hydrolysate a) on batch A (10 g of raw material), and b) on batch B (18 g of raw material).

Likewise, the soluble monosaccharide yield showed a similar trend in both processes. Furthermore, the soluble monosaccharide yield considerably increased after the enzymatic hydrolysis of the liquid hydrolysate product, confirming the presence of water-soluble oligosaccharides in the liquid products from the acid hydrolysis of switchgrass. FIGS. 4 a and b show the soluble monosaccharide yield from the carbohydrate analysis of the liquid products from both processes, as well as the soluble monosaccharide yield produced during acid hydrolysis of switchgrass and during enzymatic hydrolysis of the solid-free liquid hydrolysate. The results in FIGS. 3 and 4 show that the acid hydrolysis process is reproducible.

Figure 5:
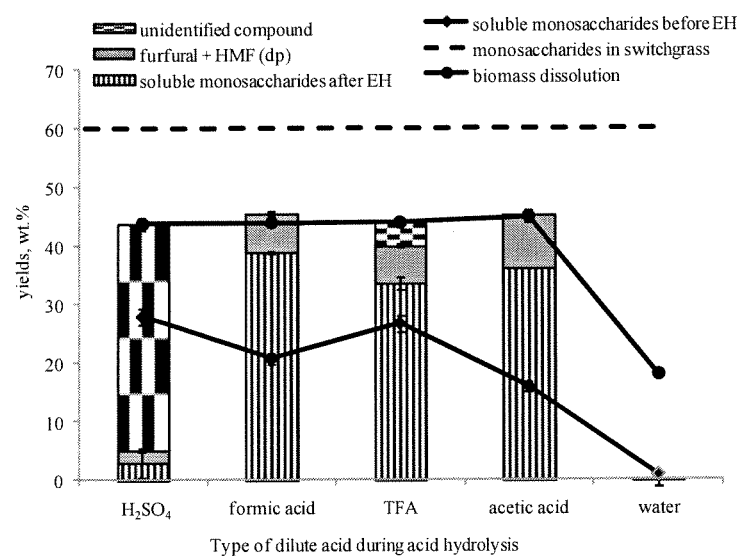
FIG. 5 shows water-soluble monosaccharide yield, degradation product yield (furfural and HMF) and unidentified compounds yield from acid hydrolysis at 150° C. and pH=1.65. The error bars represent the range of numbers obtained from multiple runs.

Efficiency of Aqueous Acid Solutions Comprising Formic Acid of the Present Invention Compared to Mineral Acid and Other Organic Acids The soluble monosaccharide content of the liquid product was quantified immediately after acid hydrolysis and after enzymatic hydrolysis of the acid hydrolysate. FIG. 5 shows the dissolution yield of switchgrass, the soluble carbohydrate yield, the degradation products yield and the yield of unidentified compounds. Here, sulfuric acid along with all the organic acids tested hydrolyzed 42-45 wt. % of the raw material (FIG. 5) at 150° C. However, the soluble monosaccharide yield in the acid hydrolysate varied depending on the acid used during the hydrolysis. After enzymatic hydrolysis, the soluble monosaccharide yield was comparable in all cases where organic acids were used. In contrast, sulfuric acid showed completely different behavior, as the soluble monosaccharide yield after enzymatic hydrolysis significantly decreased.

Figure 6:
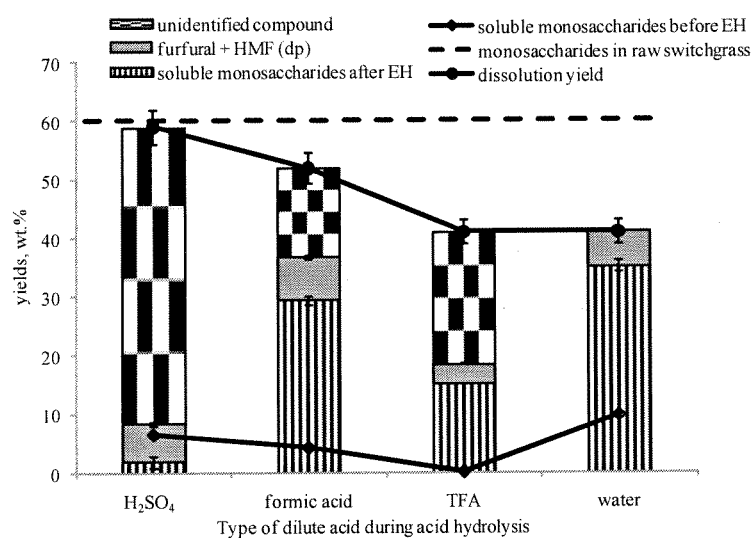
FIG. 6 shows water-soluble monosaccharide yield, degradation product yield (furfural and HMF) and unidentified compounds yield from acid hydrolysis at 200° C. and pH=1.65. The error bars represent the range of numbers obtained from multiple runs.

The treatment of switchgrass at 200° C. was also tested using mineral and organic acids. As shown in FIG. 6, sulfuric acid dissolved the largest biomass fraction, followed by formic acid, but they gave a completely different product distribution. Formic acid dissolved approximate 8 wt. % less switchgrass sawdust, but still yielded more soluble saccharides than sulfuric acid.

TFA and water showed similar biomass dissolution trends, but TFA, the strongest of the organic acids tested, produced a higher concentration of unidentified organic compounds compared to formic acid and the water control.

The liquid product of switchgrass sawdust treatment using formic acid at both 150° C. and 200° C. showed that ~24 wt. % and 28 wt. % of the monosaccharides after enzymatic hydrolysis are glucose, respectively. Contrary, the treatment with TFA at similar temperatures showed a decrease in the glucose yield from 22 wt. % to 15 wt. % with increasing treatment temperature, suggesting higher degradation of monosaccharides at high temperature when TFA was used in comparison with formic acid.

Conclusions

The above results showed that 8 wt. % formic acid ($pH_{25°C.}$=1.65) at 150° C. is capable of dissolving ~44 wt. % of the raw material which is surprisingly and unexpectedly similar to other acids. However, what is further surprising and unexpected is that higher concentrations of soluble saccharides are obtained using 8 wt. % formic acid at these reaction conditions. Biomass dissolution usually increases with increasing reaction temperature, but also usually leads to further degradation of soluble saccharides. The highest soluble saccharides yield above was achieved at 150° C. when the feedstock was treated with formic acid or acetic acid.

Surprisingly, 8 wt. % formic acid ($pH_{25° C.}$=1.65) yielded high dissolution of switchgrass sawdust at high temperature (200° C.), comparable to the dissolution yield achieved using 1.2 wt. % sulfuric acid ($pH_{25° C.}$=1.65) at similar reaction conditions. What was further surprising and unexpected was that 70% of the liquid product from acid hydrolysis with dilute formic acid was identified as soluble saccharides, HMF, and furfural, whereas only 22% of the liquid product from acid hydrolysis with sulfuric acid was identified as soluble saccharides, HMF, and furfural.

Biomass dissolution yield reached ~89% (of the total carbohydrate present) with 30 wt. % formic acid ($pH_{25° C.}$=1.08). In contrast to what may be expected, increasing the formic acid concentration further resulted in significant degradation of soluble products without substantially increasing biomass dissolution.

EXAMPLE 2

Material Balance for Two Examples of the Process

Dry switchgrass with a weight of 16.617 gm was employed as a feedstock. The theoretical yield is approximately 10 gm of sugars (~60% of dry biomass). Acid hydrolysis with an aqueous solution of 41 weight percent formic acid at 150° C. for 1 hour at a pH of 1.65 yielded 4.78 gm of monosaccharides. Enzymatic hydrolysis yielded a total of 6.98 gm monosaccharides which represents about 70% of the total sugars present in the biomass. The amount of ethanol produced was 0.09 gm per gm of dry biomass.

Figure 7:
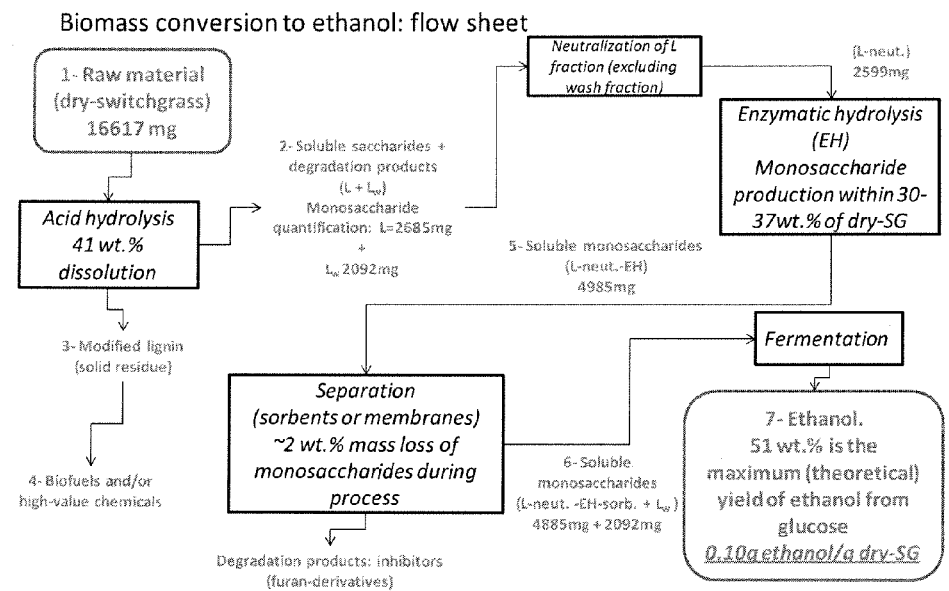
FIG. 7 show a flow sheet for one example of the process of the present inventions.

The example was repeated again using dry switchgrass with a weight of 16.617 gm as a feedstock which as described above should yield approximately 10 gm of sugars (~60% of dry biomass). This time acid hydrolysis with an aqueous solution of 41 weight percent formic acid at 150° C. for 1 hour at a pH of 1.65 also yielded 4.78 gm of monosaccharides. Enzymatic hydrolysis yielded a total of 8.17 gm monosaccharides which represents about 81% of the total sugars present in the biomass. The amount of ethanol produced was 0.11 gm per gm of dry biomass. The results are summarized in the table below and in the flow diagram at FIG. 7.

What is claimed is:

1. A process for treating a feedstock comprising holocellulose wherein the process comprises:
   a) mixing the feedstock with an aqueous acid solution of an initial $pH_{25° C.}$ of from about 1 to about 3, wherein the acid is from 1 to 30 percent by weight of the total weight of the aqueous acid solution and wherein said acid is comprised of at least or about 90% by weight of formic acid based on the total weight of the acid; and
   b) hydrolyzing the mixture under conditions sufficient to produce a product comprising monosaccharides and water-soluble oligosaccharides wherein the sum of monosaccharides and water-soluble oligosaccharides is at least or about 50% by weight of the total holocellulose in the lignocellulosic feedstock.

2. The process of claim 1 wherein the mixture of step a) has an initial $pH_{25° C.}$ of from about 1.2 to about 2.

3. The process of claim 1 wherein the acid is comprised of at least or about 95% by weight of formic acid based on the total weight of the acid.

4. The process of claim 1 wherein the acid is comprised of less than or about 15% by weight of mineral acid based on the total weight of the acid.

5. The process of claim 1 wherein the acid is from about 4 to about 20% by weight of aqueous phase and wherein said acid is comprised of at least or about 95% by weight of formic acid based on the total weight of the acid.

6. The process of claim 1 wherein at least a portion of the formic acid employed in the aqueous acid solution is produced from a renewable biomass feedstock.

7. The process of claim 1 wherein at least a portion of the formic acid employed in the aqueous acid solution is produced in a method comprising a step selected from the group consisting of acid hydrolyzing one or more carbohydrates, pyrolyzing glucose, and oxidizing one or more monosaccharides.

8. The process of claim 1 wherein the mixture is hydrolyzed at a temperature of from about 75° C. to about 225° C. for a time period of from about 30 minutes to 3 hours.

9. The process of claim 1 wherein the mixture is hydrolyzed at a temperature of from about 125° C. to about 175° C. for a time period of from about 45 minutes to 2 hours.

10. The process of claim 1 which further comprises converting at least a portion of water-soluble oligosaccharides to monosaccharides.

11. The process of claim 1 which further comprises conducting an enzymatic hydrolysis on at least a portion of the product to form an enzymatic hydrolysis product.

Acid hydrolysis using formic acid @ $pH_{25° C.}$, 150° C. for 1 h
Hastelloy Parr reactor
mass balance

| dry-switchgrass, mg | monosaccharides after AH, mg | monosaccharides after AH and after neutralization, mg | monosaccharides after EH, mg | monosaccharides after EH and after sorption, having 2% mass loss, mg | glucose after EH, mg |
|---|---|---|---|---|---|
| 16617 | from fresh liquor 2685<br>from wash = 2092 | 2599<br>— | 4985<br>— | 4885<br>— | 2931<br>314 |

| Theoretical ethanol production (including fresh liquor and wash), mg ethanol | Theoretical ethanol production, mL ethanol | Ethanol production g/g dry-sg |
|---|---|---|
| 1655 | 2.1 | 0.10 |

12. The process of claim 11 which further comprises removing at least a portion of any solids from the product prior to said enzymatic hydrolysis.

13. The process of claim 11 which further comprises fermenting at least a portion of the enzymatic hydrolysis product under suitable conditions to form ethanol, butanol, or a mixture thereof.

14. The process of claim 1 which further comprises fermenting at least a portion of the product under suitable conditions to form ethanol, butanol, or a mixture thereof.

15. A composition suitable for bioalcohol production comprising: a feedstock comprising holocellulose; and an aqueous acid solution comprising at least or about 90% formic acid of the total acid weight; wherein the composition has a $pH_{25°\,C.}$ of from about 1 to about 3; and wherein the acid is from 1 to 30 percent by weight of the total weight of the aqueous acid solution.

16. The composition of claim 15 wherein the feedstock is selected from a wood or forestry residue, municipal paper waste, algae, agricultural residue, dedicated energy crop, or a mixture thereof.

17. The composition of claim 15 wherein the lignocellulosic feedstock is selected from sawmill discards, paper mill discards, corn stover, sugarcane bagasse, switchgrass, and mixtures thereof.

18. The composition of claim 15 wherein the composition has a $pH_{25°\,C.}$ of from about 1.2 to about 2.

19. The composition of claim 15 wherein the acid of the aqueous acid solution is comprised of less than or about 15% by weight of mineral acid based on total acid weight.

20. The composition of claim 15 wherein the aqueous acid comprises from about 4 to about 20% by weight of acid and wherein said acid is comprised of at least or about 95% by weight of formic acid based on the total weight of the acid.

21. The composition of claim 15 wherein the volume/weight ratio of aqueous acid solution to feedstock is from about 5 to about 15 at 25° C.

22. The composition of claim 15 wherein the composition consists essentially of a lignocellulosic feedstock, formic acid, and water.

* * * * *